United States Patent
Liu et al.

(10) Patent No.: US 8,470,583 B1
(45) Date of Patent: Jun. 25, 2013

(54) LACTOBACILLUS STRAIN AND BACTERIOCIN

(75) Inventors: Siqing Liu, Dunlap, IL (US); Kenneth M. Bischoff, Morton, IL (US); Brian J. Wilkinson, Carlock, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 17 days.

(21) Appl. No.: 12/888,541

(22) Filed: Sep. 23, 2010

(51) Int. Cl.
*C12N 1/02* (2006.01)
*C12N 1/04* (2006.01)
*C07K 14/195* (2006.01)
*A01N 63/02* (2006.01)

(52) U.S. Cl.
USPC ............ 435/252.9; 424/93.45; 424/780; 530/350

(58) Field of Classification Search
USPC ...... 424/93.45, 780; 435/252.9, 853; 530/350
See application file for complete search history.

(56) References Cited

PUBLICATIONS

Ljungh et al. 2002. Isolation, Selection and Characteristics of *Lactobacillus paracasei* subsp. *paracasei* F19. Microbial Ecology in Health and Disease, Suppl 3, pp. 4-6.*
Lozo et al. 2007. Molecular Characterization of a Novel Bacteriocin and an Unusually Large Aggregation Factor of *Lactobacillus paracasei* subsp. *paracasei* BGSJ2-8, a Natural Isolate from Homemade Cheese. Current Microbiology, vol. 55, pp. 266-271.*
Collins et al. 1989. Deoxyribonucleic Acid Homology Studies of *Lactobacillus casei*, *Lactobacillus paracasei* sp. nov., subsp. *paracasei* and subsp. *tolerans*, and *Lactobacillus rhamnosus* sp. nov., comb. nov. International Journal of Systematic Bacteriology, vol. 39, No. 2, pp. 105-108.*
Tindall, 2008. The type strain of *Lactobacillus casei* is ATCC 393, ATCC 334 cannot serve as the type because it represents a different taxon, the name *Lactobacillus paracasei* and its subspecies names are not rejected and the revival of the name '*Lactobacillus zeae*' contravenes Rules 51b (1) and (2) of the International Code of Nomenclature of Bacteria.Opinion 82. International Journal of Systematic and Evolutionary Microbiology, vol. 58, pp. 1764-1765.*
Qin et al. 2009. *Lactobacillus paracasei* subsp. *paracasei* ATCC 25302, sequence version 1 integrated into UniProtKB/TrEMBL.on Jun. 16, 2009.*
Kojic et al. Jun. 15, 2010. Construction of a new shuttle vector and its use for cloning and expression of two plasmid-encoded bacteriocins from *Lactobacillus paracasei* subsp. *paracasei* BGSJ2-8. International Journal of Food Microbiology, vol. 140, pp. 117-124.*
Bischoff, Kenneth M., et al., "Antimicrobial susceptibility of *Lactobacillus* species isolated from commercial ethanol plants", J. Ind. Microbial Biotechnol., 2007, 34, pp. 739-144.
J. Delves-Broughton, "Nisin as a food preservative", Food Australia, 57, 12, Dec. 2005, pp. 525-527.
Twomey, Denis, et al., "Lantibiotics produced by lactic acid bacteria: structure, function and applications". Antonie van Leeuwenhoek, 82, pp. 165-185, 2002.
Field, Des, et al., "The generation of nisin variants with enhanced activity against specific Gram-positive pathogens", Molecular Microbiology 2008 69[1], pp. 218-230.

* cited by examiner

*Primary Examiner* — Jon P Weber
*Assistant Examiner* — Kailash C Srivastava
(74) *Attorney, Agent, or Firm* — John Fado; Albert Y. Tsui; Lesley Shaw

(57) ABSTRACT

The present invention relates to an isolated *Lactobacillus paracasei* bacterium, deposited as NRRL B-50314, that secretes a bacteriocin. More specifically, the bacteriocin has antibacterial activity against a range of Gram-positive bacteria, including but not limited to *Listeria monocytogenes, Staphylococcus aureus, Enterococcus faecalis*, and other *Lactobacillus* species. Additionally, the bacteriocin has antibacterial activity against methicillin resistant *Staphylococcus aureus*.

2 Claims, 5 Drawing Sheets

LACTOBACILLUS STRAIN AND BACTERIOCIN

FIELD OF INVENTION

The present invention relates to an isolated bacterium *Lactobacillus paracasei* that produces an antibacterial polypeptide. More specifically, the polypeptide has antibacterial activity against a range of bacteria, including but not limited to food-borne pathogens and methicillin-resistant strains of *Staphylococcus aureus*.

BACKGROUND OF INVENTION

Microorganisms produce a variety of compounds which demonstrate anti-bacterial properties. One group of these compounds, bacteriocins, consists of bactericidal proteins with a mechanism of action similar to ionophore antibiotics. Bacteriocins are often active against species which are closely related to the producer. Their widespread occurrence in bacterial species isolated from complex microbial communities such as the intestinal tract, the oral or other epithelial surfaces, suggests that bacteriocins may have a regulatory role in terms of population dynamics within bacterial ecosystems. Bacteriocins are defined as compounds produced by bacteria that have a biologically active protein moiety and bactericidal action (Tagg et al., Bacteriological Reviews, Volume 40, 722 256, 1976). Other characteristics may include: (1) a narrow inhibitory spectrum of activity centered about closely related species; (2) attachment to specific cell receptors; and (3) plasmid-borne genetic determinants of bacteriocin production and of host cell bacteriocin immunity. Incompletely defined antagonistic substances have been termed "bacteriocin-like substances". Some bacteriocins effective against Gram-positive bacteria, in contrast to Gram-negative bacteria, have wider spectrum of activity. It has been suggested that the term bacteriocin, when used to describe inhibitory agents produced by Gram-positive bacteria, should meet the minimum criteria of (1) being a peptide and (2) possessing bactericidal activity (Tagg et al., supra).

Lactic acid bacteria are among the most important probiotic microorganisms. They are Gram-positive, nonsporing, catalase-negative organisms devoid of cytochromes. They are anaerobic but are aerotolerant, fastidious, acid-tolerant, and strictly fermentative with lactic acid as the major end-product of sugar fermentation. Lactic acid producing bacteria include *Lactobacillus* species, *Bifidobacterium* species, *Enterococcus faecalis*, *Enterococcus faecium*, *Lactococcus lactis*, *Leuconostoc mesenteroides*, *Pediococcus acidilactici*, *Sporolactobacillus inulinus*, *Streptococcus thermophilus*, etc. These species are of particular interest in terms of widespread occurrence of bacteriocins within the group and are also in wide use throughout the fermented dairy, food and meat processing industries. Their role in the preservation and flavour characteristics of foods has been well documented. Most of the bacteriocins produced by this group are active only against other lactic acid bacteria, but several display anti-bacterial activity towards more phylogenetically distant Gram-positive bacteria and, under certain conditions, Gram-negative bacteria.

*Lactobacilli* have been extensively studied for production of antagonists. These include the well characterized bacteriocins (DeKlerk, Nature, Volume 214, 609, 1967; Upreti and Hinsdill, Antimicrob, Agents Chemother., Volume 7, 139 145, 1975; Barefoot and Klaenhammer, Antimicrob, Agents Chemother., Volume 45, 1808 1815 1983; Joerger and Klaenhammer, Journal of Bacteriology, Volume 167, 439 446, 1986, potential bacteriocin-like substances (Vincent et al., Journal of Bacterioll., Volume 78, 479, 1959), and other antagonists not necessarily related to bacteriocins (Valkil and Shahani, Bacteriology, Proc, 9, 1965; Hamdan and Milcolajeik, Journal of Antibiotics, Volume 8, 631636, 1974; Mikolajeik and Hamdan, Cultured Dairy Freducts, Page 10, 1975; and Shahani et al., Cultured Dairy Products Journal, Volume 11, 14 17, 1976).

Klaenhammer (FEMS, Microbiol, Rev., Volume 12, 39 86, 1993) has classified the lactic acid bacteria bacteriocins known to date into four major groups:

Group I: Lantibiotics which are small peptides of <5 kDa containing the unusual amino acids lanthionine and .beta.-methyl lanthionine. These are of particular interest in that they have very broad spectra of activity relative to other bacteriocins. Examples include Nisin, Nisin Z, carnocin U 149, lacticin 81, and lactocin 5. Group II-Small non-lanthionine containing peptides: a heterogeneous group of small peptides of <10 kDa. This group includes peptides active against *Listeria* spp. Group III-Large heat labile proteins of <30 kDa. Group IV-Complex bacteriocins-proteins containing additional moieties such as lipids and carbohydrates.

The lantibiotic peptide, nisin, is produced by *Lactococcus lactis*. Nisin is desired because it is a biodegradable antibacterial agent and is safe to use as a food preservative in processed dairy products. However, since nisin cannot be synthesized artificially, the only route of production is through fermentation and involves post-translational modifications.

With zero tolerance of bacterial contamination in food and feed processing, plus generally restrictive antibiotic usage, there is a need to develop a bacteriocin that can be utilized in food, feed, and medicine. Ideally, there is a need to develop a bacteriocin that has a wide range of antibacterial activity, especially against bacteria that are antibiotic resistant.

A disadvantage of conventional antibiotics is that they do not degraded easily. The remaining residue accumulates in the environment and promotes the emergence of multi-drug resistant bacterial strains. Naturally isolated polypeptides with bactericidal activities can be used as safe alternatives to synthetic antibiotics and are promising agents to effectively control bacterial infections without the disadvantage of antibiotics.

BRIEF SUMMARY OF THE INVENTION

Disclosed herewith is an isolated *Lactobacillus paracasei* bacterium that secretes a bacteriocin. More specifically, the bacteriocin has antibacterial activity against a range of Gram-positive bacteria, including but not limited to *Listeria monocytogenes*, *Staphylococcus aureus*, *Enterococcus faecalis*, and other *Lactobacillus* species. Additionally, the bacteriocin has antibacterial activity against methicillin resistant *Staphylococcus aureus*.

Disclosed herein is an isolated bacteriocin having SEQ. ID. NO. 2, wherein the bacteriocin is isolated from a *Lactobacillus paracasei* deposited with the United States Department of Agricultural, Agricultural Research Service Patent Culture Collection as Accession Number NRRL B-50314. In one embodiment of the invention, the isolated bacteriocin has antibacterial activity against *Listeria monocytogenes*. In another embodiment of the invention, the isolated bacteriocin has antibacterial activity against *Staphylococcus aureus*. In yet another embodiment of the invention, the isolated bacteriocin has antibacterial activity against *Staphylococcus aureus* that is resistant to methicillin. In yet another embodiment of the invention, the isolated bacteriocin has antibacterial activity against *Enterococcus faecalis*. In yet another embodiment of the invention, the isolated bacteriocin has antibacterial activity against *Lactobacillus* sp.

Disclosed herein is an isolated *Lactobacillus paracasei* deposited with United States Department of Agricultural, Agricultural Research Service Patent Culture Collection as Accession Number NRRL B-50314. In one embodiment of the invention, the isolated *Lactobacillus paracasei* secretes a bacteriocin having SEQ. ID. NO. 4.

BRIEF DESCRIPTION OF THE DRAWINGS

The present invention together with the above and other objects and advantages may best be understood from the following detailed description of the embodiment of the invention illustrated in the drawings, wherein.

DEPOSIT OF BIOLOGICAL MATERIAL

Figure 1A:
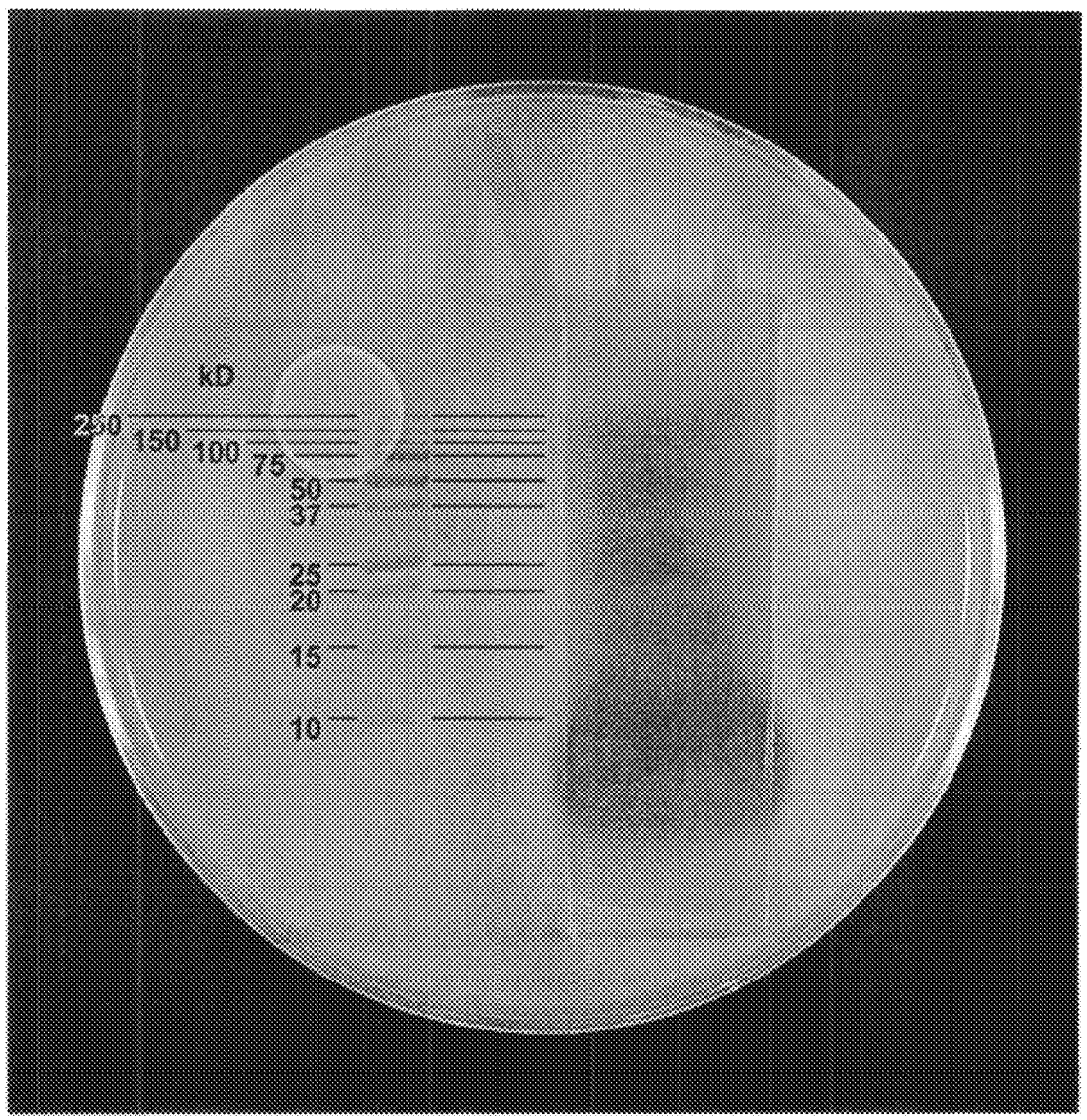
FIG. 1A is a photograph of a gel overlay assay using 15 µl of crude bacteriocin subjected to SDS PAGE (8-16% Tris-HCl ready gels from BioRad). The gel piece with a molecular weight marker was stained with BioRad Coomassie brilliant blue R-250 and de-stained overnight. The marker gel piece was then aligned in parallel with a fresh sample gel piece that was rinsed with water for 15 minutes after electrophoresis and overlaid with *Lactococcus lactis* to determine which band(s) corresponded to antibacterial activity and the molecular weight to such band(s) exhibiting activity.

Strain B-50314 was identified as a strain of *Lactobacillus paracasei* subspecies tolerans based on 16S rRNA gene sequencing. Sequence of B-50314 was 98% similar to the sequences of *Lactobacillus paracasei* subspecies tolerans Genbank strain ID 48843512. NRRL B-50314 was deposited on Sep. 10, 2009, under the provisions of the Budapest Treaty in the Agricultural Research Culture Collection (NRRL) in Peoria, Ill., and has been assigned Accession No. NRRL B-50314.

DETAILED DESCRIPTION OF THE INVENTION

Definitions

As used in the specification and claims, the singular form "a", "an" and "the" include plural references unless the context clearly dictates otherwise. For example, the term "a bacterium" includes a plurality of unicellular microorganisms of the same species.

As used in the specification and claims, an isolated bacteriocin, as used herein, means a peptide that is free of at least some of the contaminants associated with peptides occurring in a natural environment.

As used herein, the abbreviation "MSSA" is used to indicate a *Staphylococcus aureus* strain that is methicillin sensitive. As used herein, the abbreviation "MRSA" is used to indicate a *Staphylococcus aureus* strain that is methicillin-resistant. As used herein, the abbreviation "Hetero VISA" is used to indicate a *Staphylococcus aureus* strain that is heterologous Vancomycin-Intermediate Methicillin-Resistant. As used herein, the abbreviation "Homo VISA" is used to indicate a *Staphylococcus aureus* strain that is Homogeneous Vancomycin-Intermediate Methicillin-Resistant.

Bacterial Strain Identification and Isolation of Bacteriocin

A contaminating bacterial strain was isolated from a culture of *L. buchneri* B-30929 during serial transfers. A single colony was diluted and washed with sterile water, plated out on MRS, and re-streaked to obtain a pure culture that was deposited as *L. paracasei* NRRL B-50314. The strain was inoculated in 3 ml of MRS broth and incubated overnight. About 2.5 ml of the culture was then transferred to 500 mls MRS in a close-capped media bottle and incubated at 30° C. for 24 hours. Bacterial cells were removed by centrifugation and the supernatant liquid was filtered using a Nalgene disposable bottle top filter (pore size 0.8 µm) (Nalgene, Rochester, N.Y.). Aliquots of the filtrate were stored at −20° C. The filtered supernatant from culture broth of *L. paracasei* NRRL B-50314 was designated as crude bacteriocin and used for growth inhibition and gel-overlay assay. The *Lactobacillus* strains were maintained on MRS plates (Becton Dickinson, Sparks, Md.) under aerobic or anaerobic conditions (BBL GasPak anaerobic system, Becton Dickinson, Franklin Lakes, N.J.) and grown in MRS broth at either 30 or 37° C. without shaking (liquid cultures) or anaerobically (agar media).

The NRRL B-50314 strain was identified as closely related to *L. paracasei* subsp. tolerans by sequencing of 16S rRNA. Genomic DNA of *L. paracasei* NRRL B-50314 was isolated using the Gram-positive DNA purification kit (Epicentre, Madison, Wis.). Genomic PCRs were performed by using 16s rDNA primers SEQ. ID. NO 1 and SEQ. ID. NO 2. The resulting PCR fragment was then sequenced using the ABI Prism Dye Terminator Cycle Sequencing Ready Reaction Kit and the ABI Prism 310 DNA sequencer (Perkin-Elmer, Foster City, Calif.).

The nucleotide sequence of a 464 bp 16S rDNA fragment (SEQ. ID. NO. 3) shares 98% identity to that of *L. paracasei* subsp. tolerans (GenBank ID 48843512). The novel isolated strain was deposited in the ARS Patent Culture Collection as *L. paracasei* NRRL B-50314.

Peptide Digestion and Liquid Chromatography-Mass Spectrometry Identification

Figure 1B:
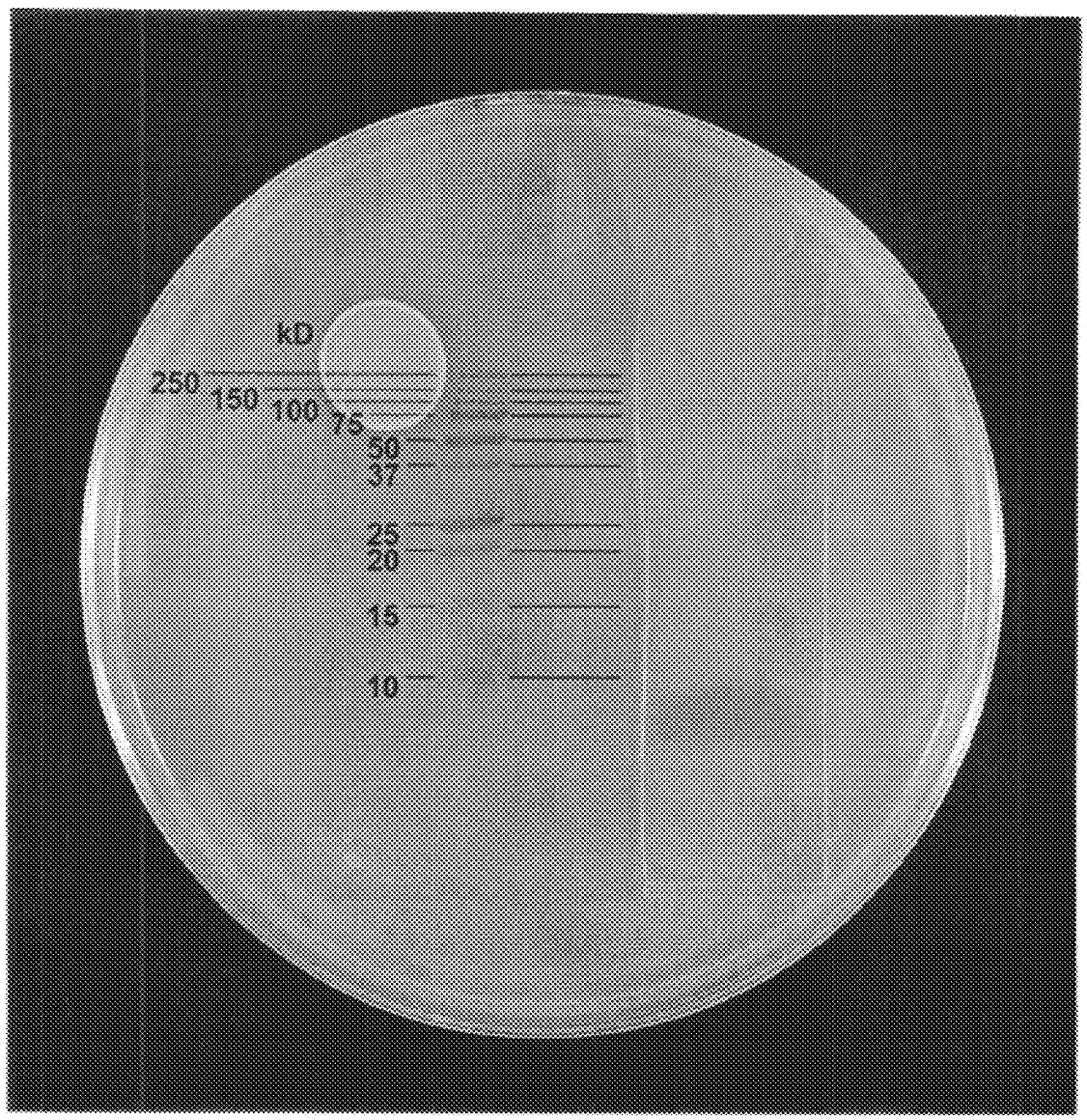
FIG. 1B is a photograph of a gel overlay assay using 15 µl of crude bacteriocin subjected to SDS PAGE (8-16% Tris-HCl ready gels from BioRad). The gel piece with a molecular weight marker was stained with BioRad Coomassie brilliant blue R-250 and de-.stained overnight. The marker gel piece was then aligned in parallel with a fresh sample gel piece that was rinsed with water for 15 minutes after electrophoresis and overlaid with *Enterococcus faecalis* to determine which band(s) corresponded to antibacterial activity and the molecular weight to such band(s) exhibiting activity.

The above mentioned SDS gel after electrophoresis was subjected to the colloidal blue staining and destaining according to the manufacture's guidelines (Invitrogen, Carlsbad, Calif.). The gel slice corresponding to the clear zone (see FIG. 1A, 1B above) were sliced out with clean razor blades and shipped to the Wistar Proteomics Facility (Wistar Institute, Philadelphia, Pa.) for identification. The samples were subjected to in gel trypsin digestion, followed by LC-ion trap mass spectrometer scanning. The final identification of the polypeptide was achieved via bioinformatics analyses of the MS/MS data against NCBI nr database of *L. paracasei* ATCC 334 genome. The peptide is identified as SEQ. ID. NO. 4:

KIQAVISIAEQQIGKPYVWGGKGPNSFDCSGLMYYAFLNGAGVNIGGWTV

PQESSGQQVSLSALQPGDLLFWGGHGSSYHVALYIGGGTMIQAPQPGENV

KYTALAYFMPDFAVRPSL

Example 1

Anti-Bacterial Activity

A gel overlay technique was used to test for antibacterial activities in cell-free culture supernatants of NRRL B-50314. A SDS-PAGE gel slice was placed over a freshly seeded lawn of indicator bacterium within a thin layer of top agar across the surface of an agar plate. The growth of bacteria distributed through the top agar produces a homogeneously turbid lawn after overnight incubation except where antibacterial agents are applied. Each sample contained 15 µl of the bacteriocin from *L. paracasei* NRRL B-50314 and 15 µl gel loading dye. A zone of inhibition was visually inspected and measured against a plurality of bacterial strains as listed in Table 1.

Example 2

Optimal Conditions for Crude Bacteriocin Production

Figure 2:
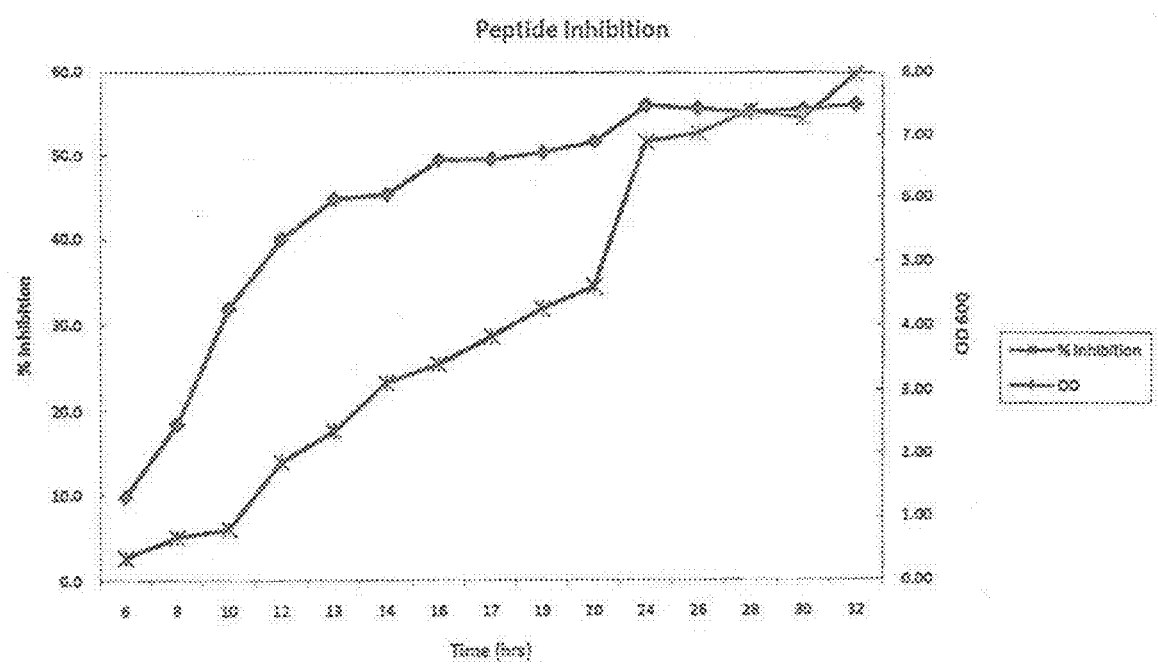
FIG. 2 is a graph of the growth pattern and production kinetics (optical density at 600 nm) of crude bacteriocin secreted by *L. paracasei* NRRL B-50314. Samples were taken every 2-4 hours and bacteriocin activity was determined by growth inhibition assay against *Lactococcus lactis* LM 0230. The inhibition activity was calculated as the average of three trials relative to a control sample in which crude bacteriocin was replaced with MRS.

Production of crude bacteriocin was assessed over a 24 hour period under conditions as described supra. The bacteriocin is produced in early exponential phase and reaches its highest level at the stationary phase as indicated in FIG. 2. Since this experiment was performed in a culture bottle without pH control, the final pH dropped to around 4.0.

The production of bacteriocin was also examined using a range of carbon/energy sources including fructose, mannose, lactose, sucrose, maltose, and cellobiose using both MK and MRSsi media. Strain B-50314 grows well in most of these carbohydrates except cellobiose and xylose.

A simplified MRS medium (designated MRSsi) was developed by varying concentrations of several components in MRS. MRSsi contains the following per liter: 5 g of casamino acids, 5 g of peptone, 5 g of yeast extract, 0.5 ml of Tween 80, 0.05 g of $MnSO_4.4H_2O$, 0.2 g of $MgSO_4.7H_2O$, 0.1 g of $CoCl_2.6H_2O$, and 5 g of sodium acetate. MK media contains the following per liter: 10 g beef extract, 5 g tryptone, 5 g yeast extract, 2 g ammonium citrate, 0.05 g of $MnSO_4.4H_2O$, 0.1 g of $MgSO_4.7H_2O$, 2 g $K_2HPO_4$, 20 g of $KH_2PO_4$, and 5 g sodium acetate. The pH of the media was adjusted to 6.5.

With a 2% inoculum, the maximum $OD_{600}$ reached up to 7.0 in 24 hours when substrates of fructose, glucose and sucrose were used. Comparing MRSsi media and MK media,

TABLE 1

Antibacterial gel overlay against indicator strains of *Staphylococcus* and *Listeria*

| Strain | Zone width (cm) | Zone height (cm) | Drug-resistance |
|---|---|---|---|
| L. lactis LM 0230 | 2.10 ± .20 | 1.70 ± .20 | |
| L. monocytogenes 10403S | 1.45 ± .03 | 1.00 ± .01 | |
| Enterococcus faecalis CK111 | 1.30 ± .10 | 0.60 ± .00 | |
| S. aureus SH1000 | 1.40 ± .01 | 1.00 ± .00 | MSSA |
| S. aureus 209P | 2.50 ± .55 | 1.20 ± .10 | MSSA |
| S. aureus DU4916S | 2.20 ± .15 | 1.40 ± .10 | MSSA |
| S. aureus 1316 P⁺M⁻ | 1.20 ± .05 | 1.10 ± .09 | MSSA |
| S. aureus 1316 P⁺M⁻ | 2.00 ± .05 | 1.40 ± .20 | MSSA |
| S. aureus COL | 1.60 ± .01 | 1.40 ± .10 | MRSA |
| S. aureus 592S | 1.50 ± .05 | 1.10 ± .10 | MRSA |
| S. aureus MM66 | 1.50 ± .15 | 1.10 ± .15 | HeteroVISA |
| S. aureus 1316 P⁻M⁺ V5 MRSA* | 1.90 ± .35 | 1.50 ± .30 | Homo VISA |
| S. aureus 1316 P⁻M⁺ V20 MRSA* | 1.40 ± .20 | 1.00 ± .00 | Homo VISA |

*The zone is not very clear.

Figure 3:
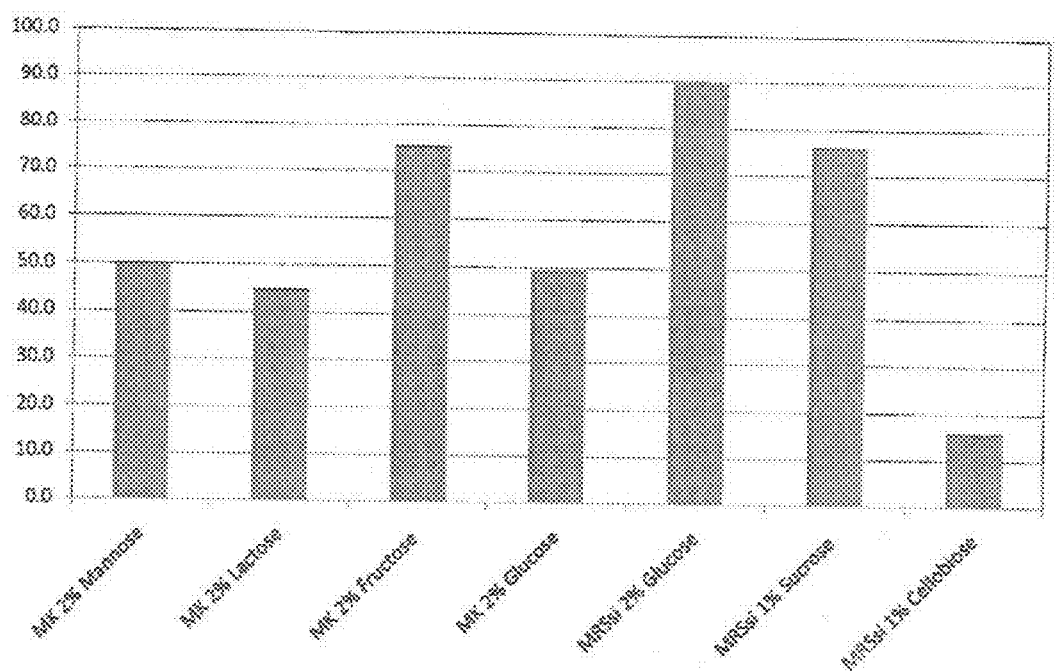
FIG. 3 is a graph of the effect of different media and carbon sources on the production of crude bacteriocin secreted by *L. paracasei* NRRL B-50314. Specifically, carbon sources of MK 2% mannose, MK 2% lactose, MK 2% fructose, MK 2% glucose, MRSsi 2% glucose, MRSsi 1% sucrose, and MRSsi 1% cellobiose were tested. The antibacterial assays were performed in 96 well plates against *L. lactis* LM 2030 with the amounts of each substrate indicated as % (g/100 ml). The substrate percentages depicted are an average of three trials.

*Staphylococcus aureus* strains were grown in tryptic soy broth (TSB) (Becton Dickinson, Sparks, Md.) or in Mueller-Hinton broth containing $CaCl_2$ (50 mg $L^{-1}$) (MHBc) (Becton Dickinson, Sparks, Md.) at 37° C. with shaking at 210 rpm. *Listeria monocytogenes* strain 104035 and *Entercoccus faecalis* CK111 were grown in brain heart infusion (BHI) broth (Becton Dickinson, Sparks, Md.) at 37° C. with shaking at 210 rpm.

cells grown in MRSsi produced more bacteriocin than in MK. As depicted in FIG. 3., 2% glucose in MRSsi growth media, 1% sucrose in MRSsi growth media, and 2% fructose in MK media are the optimal carbon sources for bacteriocin production as compared to 2% mannose, 2% lactose, and 2% glucose in MK media. Preferably, simple six carbon mono and disaccharides provide the optimal growth substrates for bacteriocin production.

Example 3

NRRL B-50314 Fermentation Products

Fermentations of *L. paracasei* NRRL B-50314 were performed in 2 liter fermentors (Biostat B, B. Braun International, Germany), at constant pH (6.0 or 5.0) controlled using 4M NaOH and 4M phosphoric acid. Fermentations were carried out by 2% inoculation at 30° C. with 100 rpm stirring. Samples were taken periodically during the course of fermentation. The concentrations of residual sugars and fermentation products, including lactate, acetate, and ethanol, were measured by HPLC using, a 300 mm Aminex HPX-87H column (Bio Rad, Richmond, Calif.) and a refractive index detector (G1362A, Agilent Technologies, Palo Alto, Calif.). Samples were run at 65° C. and eluted at 0.6 ml min$^{-1}$ with 5 mM sulfuric acid.

In addition to the bacteriocin produced and secreted into culture broth, the other major fermentation product of *L. paracasei* NRRL B-50314 is lactate. The strain can produce lactate from various substrates including glucose, fructose, sucrose, lactose, mannose and maltose as indicated in Table 2. The strain does not degrade cellobiose and is unable to use xylose, arabinose, or ribose.

TABLE 2

Table 2 HPLC analyses of the fermentation products by
*L. paracasei* NRRL B-50314 using various substrates

| Culture Media with | Fermentation products (g/100 mls or %) | | |
|---|---|---|---|
| various C sources | Lactate | Acetate* | Ethanol* |
| 2% Glucose MRSsi | 1.78 | 0.45 | 0.00 |
| 1% Sucrose MRSsi | 1.05 | 0.45 | 0.02 |
| 1% Cellobiose MRSsi | 0.37 | 0.46 | 0.03 |
| 2% Lactose MK | 1.42 | 0.37 | 0.00 |
| 2% Mannose MK | 1.40 | 0.35 | 0.00 |
| 2% Fructose MK | 1.86 | 0.34 | 0.00 |
| 2% Ribose MK | 0.89 | 0.98 | 0.00 |
| Maltose MK | 0.12 | 0.43 | 0.01 |
| 2% Glucose MK | 1.67 | 0.36 | 0.00 |
| 2% Arabinose MK | 0.09 | 0.42 | 0.00 |
| 2% Xylose MR.Ssi | 0.08 | 0.47 | 0.00 |
| 2% Arabinose MRSsi | 0.08 | 0.47 | 0.00 |
| 1% Maltose MRSsi | 1.16 | 0.50 | 0.01 |

*Both of the original MRSsi and MK media contain 0.50% (0.5 g per milliliter) acetate and negligible trace of ethanol was detected.

Example 4

Bacteriocin Activity after High Temperature Treatment

Figure 4:
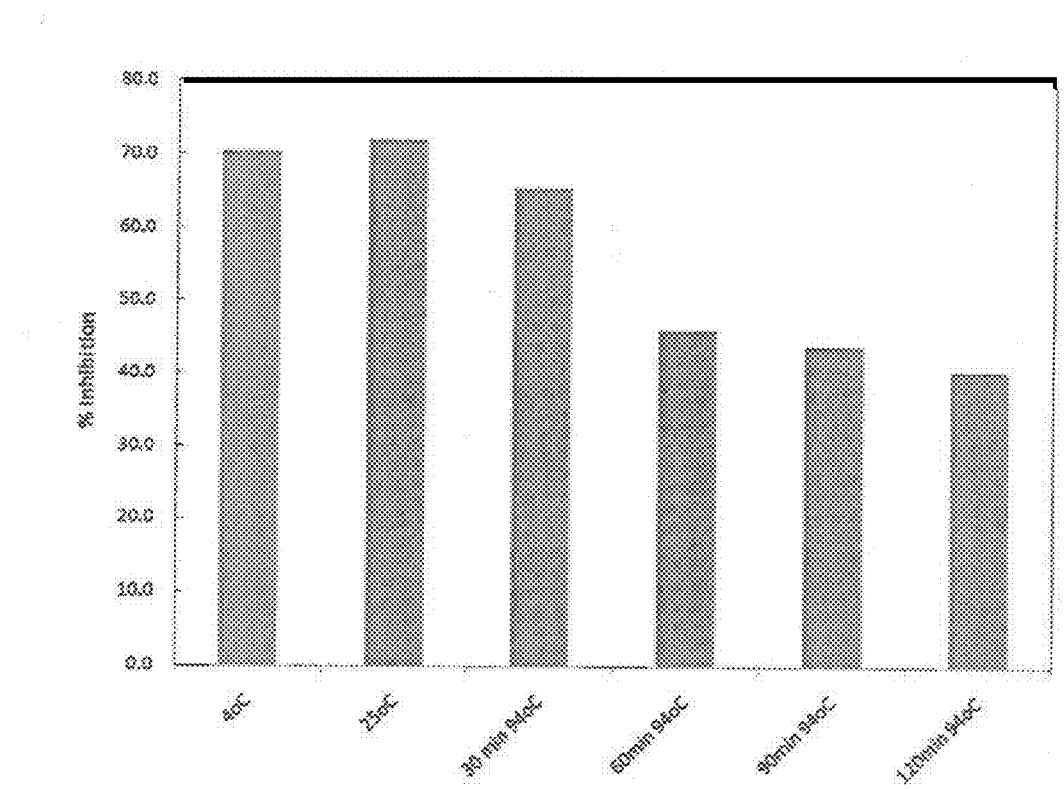
FIG. 4 Effects of high temperature treatment on antibacterial activity of crude bacteriocin. Samples were placed in a heat block at 94° C. and taken out after 30, 60, 90 and 120 minutes incubation. Growth inhibition assays were performed in 96 well plates against *L. lactis* LM 2030 and the average of three trials.

The crude bacteriocin was subjected to high temperature (94° C.) treatments ranging from 30 minutes to 120 minutes. When compared with a control sample stored at 4° C. for one week, heat treatment for greater than 60 min decreased inhibitory activity significantly, but did not abolish the inhibitory activity. The growth inhibition activity of crude bacteriocin remained effective for 30 minutes of high temperature (94° C.) treatment (FIG. 4).

Example 5

Bactericidal Activity Against *Lactococcus Lactis*

Depicted in FIG. 2 is the bactericidal activity of the crude bacteriocin from *Lactobacillus paracasei* NRRL B-50314 against *Lactococcus lactis* LM 0230. The bactericidal activities were measured by growth inhibition of *L. lactis* in well plates containing 260 µl of MRS broth, 5 µl of an overnight culture of *L. lactis*, and 15 µl of the crude bacteriocin. The bacteriocin is the supernatant of a 24 hour culture of NRRL B-50314 in MRS both after centrifugation and filtration removal of *Lactococcus paracasei* cells. The well mixture was incubated for 16 hours at 30° C. and the optical density was measured at 600 nm. Table 3 below depicts the OD and the percent activity of the *L. lactis* with respect to a MRS control sample.

TABLE 3

Table 3 OD and Percent activity of crude bacteriocin
against *Lactococcus lactis* LM0230

| Time (hours) | OD (600 nm) | Crude Bacteriocin Activity against *Lactococcus lactis* |
|---|---|---|
| 6 | 1.31 | 2.7 |
| 8 | 2.45 | 5.0 |
| 10.5 | 4.26 | 0.0 |
| 12.5 | 5.34 | 0.0 |
| 13.5 | 5.97 | 17.6 |
| 14.5 | 6.04 | 23.3 |
| 16.5 | 6.60 | 28.7 |
| 18.5 | 6.72 | 32.0 |
| 24 | 7.47 | 51.7 |
| 26 | 7.42 | 52.7 |
| 28 | 7.36 | 55.4 |
| 30 | 7.41 | 54.5 |
| 32 | 7.48 | 59.8 |

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. An isolated, biologically homogeneous *Lactobacillus paracasei* subspecies tolerans deposited with United States Department of Agricultural, Agricultural Research Service Patent Culture Collection as Accession Number NRRL B-50314.

2. The *Lactobacillus paracasei* subspecies tolerans of claim 1, wherein the *Lactobacillus paracasei* subspecies tolerans secretes a bacteriocin having a sequence of SEQ. ID. NO. 4.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Lactobacillus paracasei

<400> SEQUENCE: 1
gagagtttga tyctggctca g                                      21
```

```
<210> SEQ ID NO 2
<211> LENGTH: 21
<212> TYPE: DNA
<213> ORGANISM: Lactobacillus paracasei

<400> SEQUENCE: 2
gaaggaggtg wtccarccgc a                                              21

<210> SEQ ID NO 3
<211> LENGTH: 464
<212> TYPE: DNA
<213> ORGANISM: Lactobacillus paracasei

<400> SEQUENCE: 3
ctggcggcgt gcctaataca tgcaagtcga acgagttctc gttgatgatc ggtgcttgca    60
ccgagattca acatggaacg agtggcggac gggtgagtaa cacgtgggta acctgccctt   120
aagtggggga taacatttgg aaacagatgc taataccgca tagatccaag aaccgcatgg   180
ttcttggctg aaagatggcg taagctatcg cttttggatg gacccgcggc gtattagcta   240
gttggtgagg taatggctca ccaagcgcga tgatacgtag ccgaactgag aggttgatcg   300
gccacattgg gactgagaca cggcccaaac tcctacggga ggcagcagta gggaatcttc   360
cacaatggac gcaagtctga tggagcaacc ccccgtgagt gaagaaggct ttcgggtcgt   420
aaaactctgt tgttggagaa aaatggtcgg cagaataact gttg                   464

<210> SEQ ID NO 4
<211> LENGTH: 118
<212> TYPE: PRT
<213> ORGANISM: Lactobacillus paracasei

<400> SEQUENCE: 4

Lys Ile Gln Ala Val Ile Ser Ile Ala Glu Gln Gln Ile Gly Lys Pro
1               5                   10                  15

Tyr Val Trp Gly Gly Lys Gly Pro Asn Ser Phe Asp Cys Ser Gly Leu
            20                  25                  30

Met Tyr Tyr Ala Phe Leu Asn Gly Ala Gly Val Asn Ile Gly Gly Trp
        35                  40                  45

Thr Val Pro Gln Glu Ser Ser Gly Gln Gln Val Ser Leu Ser Ala Leu
    50                  55                  60

Gln Pro Gly Asp Leu Leu Phe Trp Gly Gly His Gly Ser Ser Tyr His
65                  70                  75                  80

Val Ala Leu Tyr Ile Gly Gly Gly Thr Met Ile Gln Ala Pro Gln Pro
                85                  90                  95

Gly Glu Asn Val Lys Tyr Thr Ala Leu Ala Tyr Phe Met Pro Asp Phe
            100                 105                 110

Ala Val Arg Pro Ser Leu
        115
```